United States Patent
Leach et al.

(10) Patent No.: US 6,441,167 B1
(45) Date of Patent: Aug. 27, 2002

(54) CINOXACIN LANTHANIDE CHELATES AND THEIR USE AS BIOMOLECULAR PROBES

(75) Inventors: Colin Andrew Leach, Stevenage; Keith James Millan Moore, Welwyn; Steven James Stanway, Thundridge, all of (GB)

(73) Assignee: SmithKline Beecham plc, Brentford (GB)

(*) Notice: Subject to any disclaimer, the term of this patent is extended or adjusted under 35 U.S.C. 154(b) by 0 days.

(21) Appl. No.: 09/720,172
(22) PCT Filed: Jun. 18, 1999
(86) PCT No.: PCT/EP99/04277
§ 371 (c)(1), (2), (4) Date: Feb. 16, 2001
(87) PCT Pub. No.: WO99/66780
PCT Pub. Date: Dec. 29, 1999

(30) Foreign Application Priority Data

Jun. 25, 1998 (GB) ............................................... 9813776

(51) Int. Cl.$^7$ .................... C07D 237/26; C07D 237/36; C07D 487/00; C12Q 1/68
(52) U.S. Cl. ........................................... 544/234; 435/6
(58) Field of Search ............................... 435/6; 544/234

(56) References Cited

U.S. PATENT DOCUMENTS

| | | | | |
|---|---|---|---|---|
| 4,379,929 A | * | 4/1983 | Conrad et al. | 544/234 |
| 5,571,897 A | | 11/1996 | Takalo et al. | 534/15 |
| 5,622,821 A | * | 4/1997 | Selvin et al. | 435/6 |
| 5,639,615 A | | 6/1997 | Selvin et al. | 435/6 |
| 5,656,433 A | | 8/1997 | Selvin et al. | 435/6 |

FOREIGN PATENT DOCUMENTS

| | | |
|---|---|---|
| DE | 20 65 719 | 3/1975 |
| DE | 207 098 | 2/1984 |
| WO | WO 96/00901 | 1/1996 |

OTHER PUBLICATIONS

Izumi, et al., "Protein Binding of Quinolonecarboxylic Acids. II. Spectral Changes on the Interaction of Cinoxacin, Nalidixic Acid and Pipemidic Acid with Human and Rat Albumins", (1989), Chem. Pharm. Bull., 37(3), pp. 746–752.

* cited by examiner

Primary Examiner—Jezia Riley
(74) Attorney, Agent, or Firm—Yuriy P. Stercho; Stephen Venetianer; Charles M. Kinzig

(57) ABSTRACT

This invention relates to novel compounds that can complex with lanthanide cations, processes for their preparation and the use of the resulting lanthanide chelates as biomolecular probes.

5 Claims, 4 Drawing Sheets

CINOXACIN LANTHANIDE CHELATES AND THEIR USE AS BIOMOLECULAR PROBES

This is a 371 of International Application PCT/EP99/04227, filed Jun. 18, 1999, which claims benefit from the following Provisional Application No. GB 9813776.3, filed Jun. 25, 1998.

This invention relates to novel compounds that can complex with lanthanide cations processes for their preparation and the use of the resulting lanthanide chelates as biomolecular probes. In particular, this invention relates to complexing compounds which contain novel photosensitizers and can produce long-lived fluorescence for use in bioaffinity assays, especially those of HTRF (homogeneous time-resolved fluorescence).

With the growth of combinatorial chemistry and high-throughput screening, particularly within the pharmaceutical industry, the requirement for biological assays has dramatically increased. Traditional assay technologies, which are often based on radioisotope labels, are unable to achieve the desired throughput whilst simultaneously reducing assay volumes. As a result of the deficiencies inherent in traditional methodologies there has been a shift towards the use of new technologies based on fluorescence. Such techniques can have a number of advantages over radioactive assays, but ability to automate, ease of use, miniaturisability, and sensitivity are of particular importance. One of the primary technologies utilised is homogeneous time resolved fluorescence energy transfer (HTRF). This proximity based method requires the use of a fluorescent donor moiety covalently attached to the interacting molecules, either directly or via labelled antibodies or labelled streptavidin which, when in proximity with a second fluorescent or chromophoric label (the acceptor), leads to a modulation of the fluorescence properties of the donor. Such methods provide useful information about the structure, conformation, relative location and/or interactions of macromolecules. In particular. HTRF has widespread application in high throughput screening of molecular interactions and enzymes using proteins, ligands and substrates labelled with donors and acceptors.

Traditional fluorescent labels of organic dyes such as fluoresceins and rhodamines have long been employed as bioanalytical tools in immunoassays. Lanthanide chelates are more recently developed fluorescence agents and have been found to possess properties which make them very suited as potential labels in the bioassay field. Thus, the lanthanide chelates are capable of giving long-lived and longer wavelength fluorescent emissions upon excitation. Through time-delay measurements they have demonstrated clear advantages over conventional fluorescent labels in terms of experiencing less quenching and background interference while exhibiting increased detection sensitivity. In addition to these advantages, many lanthanide chelates have improved solubility properties and are able to efficiently transfer energy from their excited states to neighbouring acceptor molecules. As such they are ideal agents for HTRF use especially for developing high-throughput automated and miniaturized binding assays with the inclusion of immunoassays, DNA hybridization assays, receptor binding assays, enzyme assays. cell-based assays. immunocytochemical or immunohistochemical assays.

Lanthanide chelates typically comprise a chelating group which binds the lanthanide and an organic sensitiser group. The sensitiser group has the function of absorbing light and transferring energy to the lanthanide. It thereby overcomes the inherently low absorbance of the lanthanide ions. Such chelates have been extensively reviewed, for example in Li and Selvin (J. Am. Chem. Soc (1995) 117, 8132–8138). Lanthanide chelator groups comprising a plurality of polyaminocarboxylate groups are commonly used. European patent EP0203047B1 discloses fluorescent lanthanide chelates comprising "TEKES" (4-(4-isothiocyanatophenylenthynyl-2,6-{N,N-bis(carboxymethyl)aminomethyl]-pyridine) type photosensitizers. Patent application WO 96/00901A1 discloses lanthanide chelates comprising the chelator group DTPA (diethylenetriaminepentacetic acid) covalently bonded to a coumarin or quinolone-like sensitisers. Heyduck and Heyduck (Anal. Biochem. (1997) 248, 216–227) describe compounds of similar structure to those of WO 96/00901 but differ in that they possess a thiol-reactive pyridyl disulphide moiety which allows covalent attachment to macromolecules.

It is widely recognised that the role of the sensitiser group is of fundamental importance in that they impart to the chelates different physicochemical properties pertaining to excitation wavelength, lifetime, quantum yield, quenching effect, complex stability, photostability, solubility, charge, nonspecific protein interaction, biocoupling efficiency and ease of preparation. It is advantageous to have a diversity of novel fluorescent probes to use and develop HTRF assays. There is consequently a need for more and better ways of fluorescently labelling assay components.

The present invention therefore provides, in a first instance, a lanthanide chelate comprising one or more sensitiser group(s) covalently attached to a lanthanide chelating group which is characterised in that the sensitiser group is a group of formula (I)

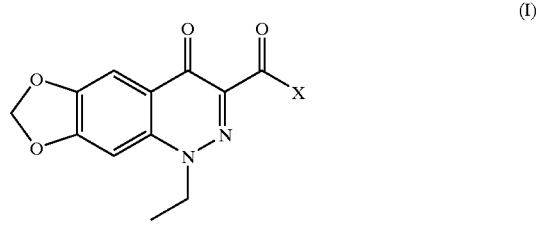

(I)

where X is a group that couples the said sensitiser group to the said chelating group.

Suitably X is any group that is capable of covalently linking the sensitiser group with the chelator group and, at the same time, does not affect the ability of the chelating group to bind the lanthanide cation. Preferably X is a group —NH(CH$_2$)pNH— in which p is 2, 3 or 4 and which forms an amide bond with the chelating group. Most preferably X is a group —NH(CH$_2$)$_2$NH—.

Preferably the lanthanide chelate contains 1 or 2 sensitiser group(s) of formula (I).

Where used herein the term [lanthanide] chelating group is used to describe a group that is capable of forming a high affinity complex with lanthanide cations such as Tb$^{3+}$, Eu$^{3+}$, Sm$^{3+}$, Dy$^{3+}$. Any fluorescent lanthanide metal can be used in the chelates of this invention but it is expected that chelates containing europium or terbium will possess the best fluorescent properties. Most preferably the lanthanide metal is europium.

Suitable examples of chelating groups include those described in WO 96/00901. Preferably the chelating group will be either DTPA (diethylenetriaminepentacetic acid) or TTHA (triethylenetetraaminehexacetic acid), that is to say compounds of the formula (II)

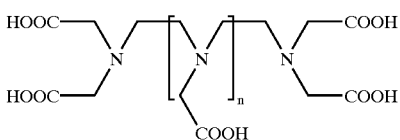

(II)

where n=1 (DTPA) or n=2 (TTHA). Both DTPA and TTHA are well known in the art and are available from commercial suppliers. Alternatively the chelating group is a compound of formula (III).

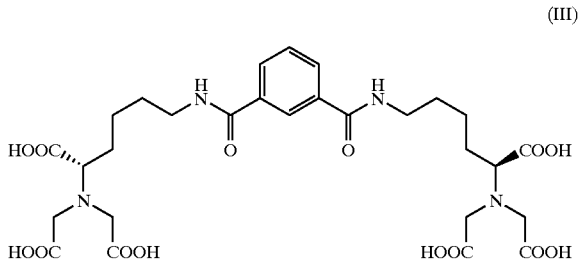

(III)

A compound of formula (III) may be prepared by reaction of the corresponding N,N-α-bis(carboxymethyl)-L-lysine with isophthalic acid activated by O—(N-succinimidyl)-1,1,3,3-tetramethyluronium tetrafluoroborate.

Typically a compound of formula (IV)

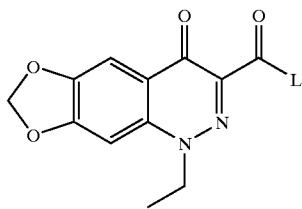

(IV)

in which L is a group —NH(CH$_2$)pNH$_2$ where p is 2, 3 or 4 would be used in the preparation of a lanthanide chelate of formula (I). A compound of formula (IV) can be prepared from Cinoxacin (commercial product supplied by Sigma) by forming its acid chloride derivative and then reacting with an appropriate alkylene diamine reagent. A compound of formula (IV) in which p is 3 or 4 is believed to be novel.

Compounds of structure (I) have desirable spectral properties in solution, but to use them in a biological assay it is necessary to attach them to the molecules such as proteins, nucleic acids, lipids, carbohydrates or peptides. Reagents containing reactive groups suitable for derivatising macromolecules will also form part of the invention. The invention therefore provides, in a further aspect, for a lanthanide chelate of structure (I) further comprising a linker group wherein the linker group is either a group of formula (V)

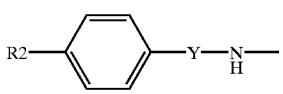

(V)

in which Y is CH$_2$, CH$_2$CH$_2$ or —CH$_2$CH(COOH)— and R$^2$ is a reactive group which is suitable for derivatising macromolecules; or the linker group is a group of formula (VI)

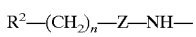—(CH$_2$)$_n$—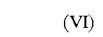—NH—  (VI)

in which n is 1 to 5, Z is a bond or a group —CH$_2$CH (COOH)— and R$^2$ is as defined for formula (V).

For groups of formula (V) and (VI) the point of attachment to the chelating group is via the amine functionality, thus forming an amide bond. Compounds of structure (V) and (VI) can be prepared from compounds of structure (I) by reaction of the mixed anhydride of (I) with the appropriate amine.

It will be appreciated by those skilled in the art that lanthanide chelates comprising linker groups of formula (V) or (VI) can, rather than labelling the target macromolecule directly, be alternatively used to label streptavidin or an antibody, which in turn binds to the target macromolecule. In such circumstances the group R$^2$ contains an epitope for an antibody or a ligand for other proteins to be used for indirect bioconjugation.

Typically the group R$^2$ is an amine reactive group, a thiol reactive group or a photoactivatable reactive group. Suitable examples of amine reactive group are those that can covalently couple with an amine functionality on a macromolecule and includes groups such as isothiocyanate (NCS) and the chlorotriazine of structure (VII);

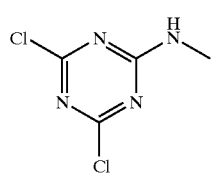

(VII)

Suitable examples of thiol reactive group are those that can covalently couple with a thiol functionality on a macromolecule and includes groups such as iodoacetamide (—NHCOCH$_2$I) and the maleimide of structure (VIII)

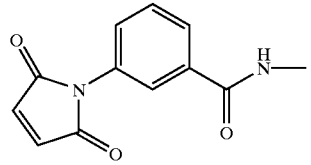

Suitable examples of a photoactivitable reactive groups include the azide of structure (IX) or of structure (X).

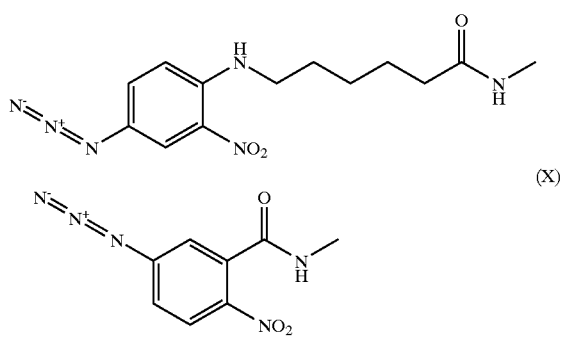

Conjugation of such chelates onto biomolecules are typically performed by incubating the reactive chelate, either in the absence or presence of the lanthanide ion, with the target molecule of interest, typically a biomolecule under conditions where the reactive groups of the target molecule are derivatised with the chelate. The reactions are terminated by quenching with an excess of a reagent with the same reactive functionality as the target molecule. If not already present in the chelate, excess lanthanide is added to the quenched reaction mixture. The purified target-chelate-lanthanide ion complex is typically obtained by preparative gel filtration, ion exchange, reverse phase or other chromatographic procedures to remove the excess chelate and, where appropriate, the lanthanide ion from the labelled target molecule.

HTRF assays are typically performed whereby the enzyme reaction or molecular interaction of interest is configured to ensure that the specific activity under investigation leads, either directly or indirectly, to a change in the mean distance between the lanthanide-chelate-target molecule and another molecule which, either itself or via conjugation to another entity (the acceptor), results in a modulation of the optical properties of the lanthanide ion or of the acceptor.

For example, target molecules are labelled directly with lanthanide chelates onto amine (Lys, N-termini), thiol (Cys), His, or Tyr residues in proteins or alternatively indirectly through antibodies, protein A or G, or streptavidin which are themselves labelled with lanthanide chelates. Acceptor molecules, such as reactive blue 4 or phycobiloproteins such as allophycocyanin, can be conjugated either directly onto the co-target of interest or indirectly via standard heterobifunctional cross linking chemistry onto, for example, streptavidin, antibodies or protein A/G.

The extent of energy transfer between the donor and acceptor can be determined either by monitoring changes in the radiative lifetime of the donor and/or acceptor e.g. using a time resolved fluorescence instrument or by measuring the time gated change in total sample intensity e.g. using a time gated fluorescence mictotitre plate reader.

The following Descriptions and Examples serve to illustrate the invention

GENERAL EXPERIMENTAL DETAILS

All analytical HPLC was performed on an Hichrom KR100-5C8 column using a gradient of 5 to 50% MeCN in 0.1% trifluoroacetic acid over 10 minutes. Peaks were characterised by online UV spectra (Hewlett-Packard 1050 diode array detector) as well as retention time. Preparative HPLC was performed on a Dynamax-60A $C_{18}$ column using a gradient of 10 to 80% MeCN in 0.1% trifluoroacetic acid over 10 minutes. For each compound comprising a chelating group the major regioisomer was as shown. However, minor isomers are also formed and these are included within the scope of the invention.

Description 1
Preparation of N-(2-Aminoethyl)cinoxacin amide (D1)

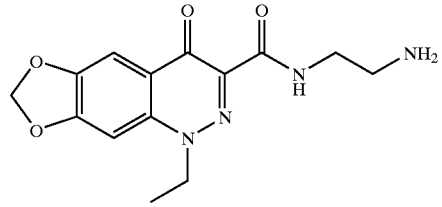

Thionyl chloride (40 ml) was added to cinoxacin (1.0 g, 3.81 mmol) in a flame dried flask under an atmosphere of argon and the resultant slurry was stirred at room temperature until the cinoxacin had dissolved (ca. 30 minutes). Excess thionyl chloride was removed under reduced pressure excluding any moisture, and the resultant yellow solid was diluted with chloroform (50 ml). The slurry was added dropwise to a solution of ethylene diamine (2 ml) in chloroform (50 ml) over a period of 30 minutes at 0° C. and then stirring was continued for a further 30 minutes at room temperature. The reaction was quenched by the addition of water and the resultant solution partitioned between chloroform and water. The aqueous phase was extracted with chloroform (4x) and the combined organic phase dried (MgSO$_4$) and the solvent removed under reduced pressure to afford a yellow solid. The residue was purified by medium pressure chromatography (Biotage flash 40S, 4.0×7.0 cm, 9:1 CH$_2$Cl$_2$/2M NH$_3$ in MeOH) to afford the title compound as a yellow solid (608 mg, 52%). HPLC (analytical): retention time=4.6 minutes; UV ($\lambda_{max}$)260, 360 nm.

$^1$H-NMR (250 MHz, CD$_3$OD): 7.66 (1H, s), 7.45 (1H, s), 6.25 (2H, s), 4.70 (2H, q, J=7 Hz), 3.60 (2H, t, J=6.5 Hz), 2.95 (2H, t, J=6.5 Hz), 1.55 (3H, t, J=7 Hz). (APCI$^+$): 305.2 (M+H$^+$, 53%).

Description 2
Preparation of Cinoxacin-DTPA (D2)

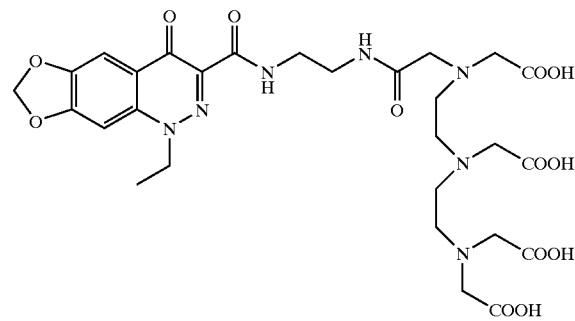

Diethylenetriaminepentacetic dianhydride (704 mg, 1.97 mmol) was dissolved in N,N-dimethylformamide (anhydrous) with stirring under an atmosphere of argon (ca 1 hour). To the resultant solution was added N-(2-aminoethyl)cinoxacin amide (D1) in a single portion and stirring continued for a further 4 hours. The reaction was quenched by the addition of water (5 ml) and the solvent removed under reduced pressure. The residue was diluted with water/methanol (1:1, 10 ml) and the indigestible solid removed by centrifugation. The remaining solution was purified by reverse phase preparative HPLC to afford the title compound, after freeze drying, as a colourless solid (247 mg, 74%).

HPLC (analytical): retention time=4.76 minutes; UV ($\lambda_{max}$) 260, 360 nm. HPLC (preparative): retention time= 5.63 minutes.

$^1$H-NMR (400 MHz, DMSO-d$_6$): 9.97 (1H, t, J=5.5 Hz), 8.15 (1H, t, J=5.5 Hz), 7.64 (1H, s), 7.54 (1H, s), 6.30 (2H, s), 4.59 (2H, q, J=7 Hz), 4.34 (2H, s), 3.53–3.17 (16H, m), 3.06 (4H, d, J=5.5 Hz), 1.40 (3H, t, J=7 Hz).

MS (ES$^+$) 680 (M+H$^+$, 25%), 702 (M+Na$^+$, 55), 718 (M+K$^+$, 100).

Description 3
Preparation of Cinoxacin-DTPA-APA (D3)

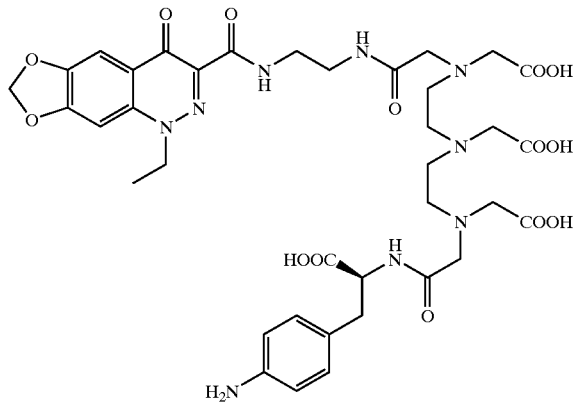

Iso-butylchloroformate (24 ul, 0.188 mmol) was added to a solution of cinoxacin-DTPA (D2) (122 mg, 0.8 mmol) in N,N-dimethylformamide/triethylarnine (3:1 v/v, 4 ml) at 0° C. under an atmosphere of argon and the reaction stirred for 15 minutes.

p-Aminophenylalanine (APA) (32 mg, 0.18 mmol) was added in a single portion and the solution stirred at room temperature for 4 hours. The reaction was quenched by the addition of water (2 ml) and the solvent removed under reduced pressure. The residue was dissolved in water/methanol and purified by reverse phase preparative HPLC to afford, after freeze drying, a colourless solid (98 mg, 65%).

HPLC (analytical): retention time=4.89 minutes: UV ($\lambda_{max}$) 258, 355 nm. HPLC (preparative): retention time= 5.47 minutes $^1$H-NMR (400 MHz, DMSO-d$_6$): 9.97 (1H, m), 8.31 (1H, m), 8.19 (1H, m), 7.64 (1H, s), 7.54 (1H, s), 7.17 (2H, m), 6.81 (2H, m), 6.30 (2H, s), 4.58 (2H, q, J=7 Hz), 4.22 (2H, s), 3.52–2.83 (25H, m), 1.58 (3H, t, J=7 Hz). MS (ES+) 842 (M+H$^+$, 25%), 864 (M+Na$^+$, 40), 880 (M+K$^+$, 100).

Description 4
Preparation of Cinoxacin-DTPA-Lysine (D4)

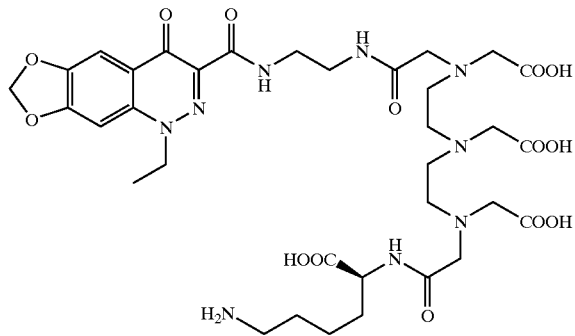

Iso-butylchloroformate (35 ul, 0.269 mmol) was added to a solution of cinoxacin-DTPA (D2) (166 mg, 0.244 mmol) in N,N-dimethylformamide/triethylantine (3:1 v/v, 6 ml) at 0° C. under an atmosphere of argon and the reaction stirred for 15 minutes N-ε-(tertbutoxycarbonyl)-(L)-lysine (78 mg, 0.318 mmol) was added in a single portion and the solution stirred at room temperature for 3 h. The reaction was quenched by the addition of water (2 ml) and the solvent removed under reduced pressure. To the residue was added dry chloroform (10 ml), to afford a suspension, which was treated with trifluoroacetic acid (200 ul). Upon dissolution of the suspension stirring was continued at room temperature for 2 hours. The solvent was removed under reduced pressure and the residue purified by reverse phase preparative HPLC to afford the title compound, after freeze drying, as a colourless solid (122 mg, 62%). HPLC (analytical): retention time=4.67 minutes; UV ($\lambda$ max) 258, 355 nm. HPLC (preparative): retention time=5.45 minutes.

MS (ES+) 808 (M+H$^+$, 32%), 830 (M+Na$^+$, 30), 846 (M+K$^+$, 100).

Description 5
Preparation of Cinoxacin-DTPA-APA-chlorotriazine (D5)

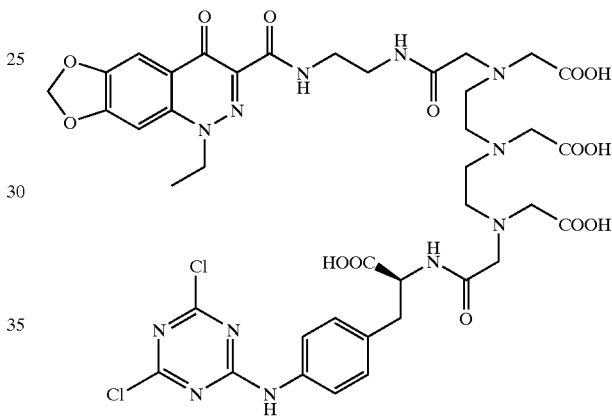

Cyanuric chloride (8.6 mg. 0.047 mmol) was added to a slurry of cinoxacin-DTPA-APA (D3) (28 mg,, 0.033 mmol) and di-iso-propyl(ethyl)amine (8 ul, 0.047 mmol) in chloroform (3 ml) under an atmosphere of argon and the reaction stirred at room temperature for 3 hours. The reaction was diluted with methanol (3 ml) and solution purified by reverse phase preparative HPLC to afford the title compound as an off white solid (17 mg, 52%).

HPLC (analytical): retention time=7.83 minutes; UV ($\lambda$ max) 260, 275, 355 nm. HPLC (preparative): retention time=7.74 minutes.

MS (ES+) 989 (M+H$^+$, $^{35}$Cl, 100%), 991 (M+H$^+$, $^{35}$Cl $^{37}$Cl, 85%), 993 (M+H$^+$, $^{37}$Cl, 25%).

The chlorotriazine was confirmed to be amine-reactive by treatment of a small portion with ethylene diamine in N,N-dimethylformamide, giving a new product with an HPLC (analytical) retention time of 5.74 mins.

Description 6
Preparation of Cinoxacin-DTPA-APA-Isothiocyanate (D6)

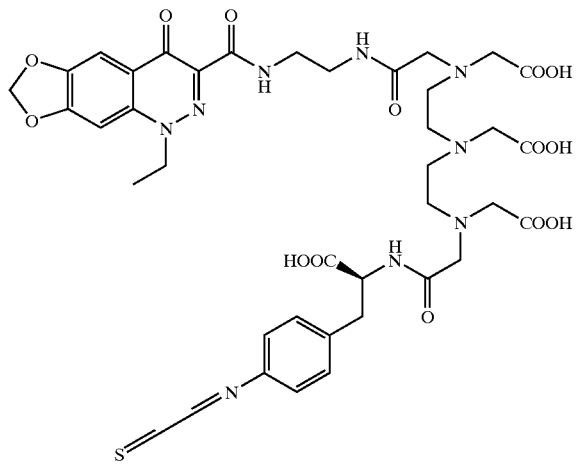

Thiophosgene (2 ul, 0.027 mmol) was added to a solution of cinoxacin-DTPA-APA (D3) (16 mg, 0.019 mmol) in chloroform/di-iso-propyl(ethyl)amine (10:1 v/v, 2.2 ml) and the resultant dark red solution stirred at room temperature under argon for 30 minutes. The reaction was diluted with methanol and purified directly by reverse phase preparative HPLC to afford the title compound as an off white solid (5.3 mg, 33%). HPLC (analytical): retention time=8.25 minutes: UV ($\lambda$ max) 258, 355 nm. HPLC (preparative): retention time=7.96 minutes.

MS (ES+) 884 (M+H$^+$, 22%), 906 (M+Na$^+$, 25), 922 (M+K$^+$, 100).

Description 7
Preparation of Cinoxacin-DTPA-lysine-azide (D7)

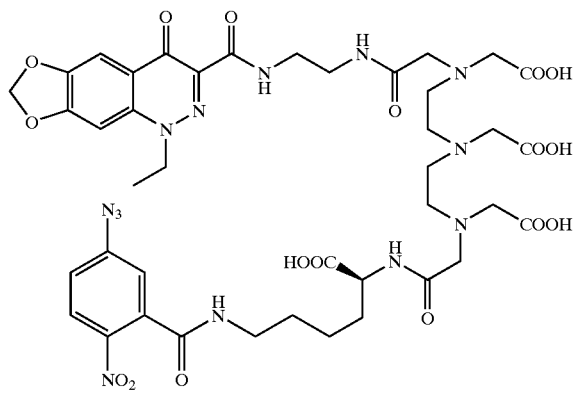

N-(5-azido-2-nitrobenzoyloxy)succinimide (15 mg, 0.050 mmol) was added to a solution of cinoxacin-DTPA-lysine (D4) (20 mg, 0.025 mmol) in chloroform/di-iso-propyl (ethyl)amine (10:1 v/v, 3.3 ml) and the resultant solution stirred at room temperature under argon for 3 hours. The reaction was diluted with methanol and purified directly by reverse phase preparative HPLC to afford the title compound as an pale yellow solid (21 mg, 85%). HPLC (analytical): retention time=6.92 minutes; UV ($\lambda$ max) 258, 355 nm. HPLC (preparative): retention time=7.24 minutes.

MS (ES+) 998 (M+H$^+$, 50%).

Description 8
Preparation of Cinoxacin-DTPA-Lysine-Iodoacetamide (D8)

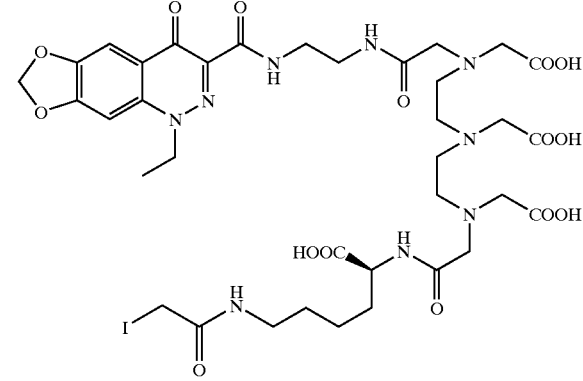

Iodoacetic anhydride (15 mg, 0.042 mmol) was added to a solution of cinoxacin-DTPA-lysine (D4) (22.5 mg, 0.028 mmol) in chloroform/di-iso-propyl(ethyl)amine (10:1 v/v. 2.2 ml) and the resultant solution stirred at room temperature under argon for 5 hours. The reaction was diluted with methanol and purified directly by reverse phase preparative HPLC to afford the title compound, after freeze drying, as an yellow/brown solid (10 mg, 37%). HPLC (analytical): retention time=5.91 minutes; UV ($\lambda$ max) 258, 355 nm. HPLC (preparative): retention time=6.31 minutes.

MS (ES+) 848 (M−I$^+$, 100%).

Description 9
Preparation of Cinoxacin-DTPA-Lysine-Maleimide (D9)

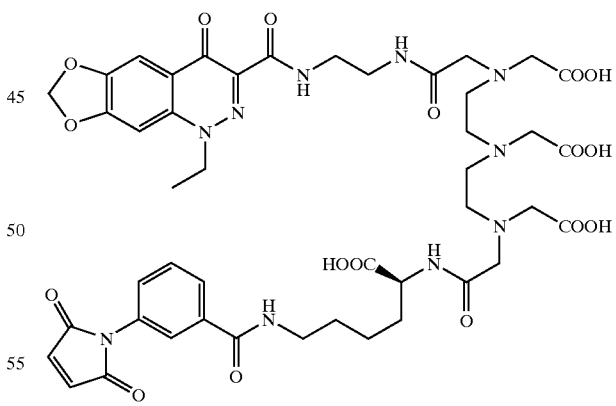

3-Maleimidobenzoic acid-N-hydroxy-succinimide ester (15 mg, 0.047 mmol) was added to a solution of cinoxacin-DTPA-lysine (D4) (19 mg, 0.024 mmol) in chloroform/di-iso-propyl(ethyl)amine (10:1 v/v, 2.2 ml) and the resultant solution stirred at room temperature under argon for 3 hours. The reaction was diluted with methanol and purified directly by reverse phase preparative HPLC to afford the title compound as an off white solid (17 mg, 72%). HPLC (analytical): retention time=6.48 minutes: UV (λ max) 258, 355 nm. HPLC (preparative): retention time=6.85 minutes.
MS (ES+) 1007 (M+H$^+$, 20%).

Description 10
Preparation of Cinoxacin-TTHA and (Cinoxacin)$_2$-TTHA (D10(a) and D10(b))

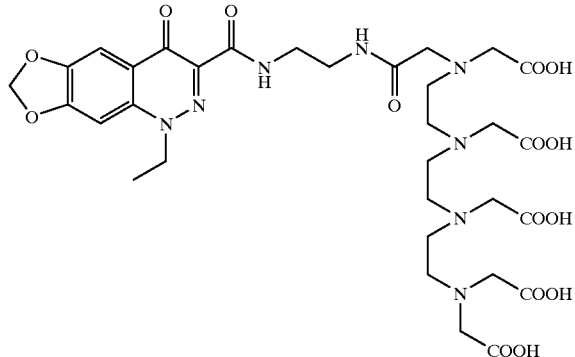

Triethylenetetraminehexacetic acid (155 mg, 0.313 mmol) was dissolved in N,N-dimethylformamide (10 ml, anhydrous) and triethylamine (3 ml) with stirring under an atmosphere of argon (ca 3 hours). To the resultant solution was added O—(N-succinimidyl)-1,1,3,3-tetramethyluronium tetrafluoroborate (123 mg. 0.408 mmol) and stirring continued for a 15 minutes at 0° C. prior to the addition of N-(2-aminoethyl)cinoxacin amide (D1) (57 mg, 0.188 mmol). After stirring for 3 hours at room temperature the reaction was quenched by the addition of water (5 ml) and the solvent removed under reduced pressure. The residue was diluted with water/methanol (1:1, 10 ml) and the indigestible solid removed by centrifugation. The remaining solution was purified by reverse phase preparative HPLC to afford the title compounds, after freeze drying, as colourless solids.

Cinoxacin-TTHA (D10(a))—Shown in Structure Above
(80 mg, 32%) HPLC (analytical): retention time=4.65 minutes, UV (λ max) 260, 360 nm.
HPLC (preparative): retention time=5.62 minutes.
$^1$H-NMR (400 MHz, DMSO-d$_6$): 9.99 (1H, t, J=5.5 Hz), 8.40 (1H, m), 7.66 (1H, s), 7.55 (1H, s), 6.32 (2H, s), 4.61 (2H, q, J=7Hz), 3.90–3.00 (26H, m), 1.41 (3H, t, J=7 Hz).
MS (ES+)781 (M+H$^+$, 10%), 803 (M+Na$^+$, 18), 819 (M+K$^+$, 19).

(Cinoxacin)$_2$-TTHA (D10(b))
(8 mg, 5%) HPLC (analytical): retention time=5.89 minutes; UV (λ max) 260, 360 nm.
HPLC (preparative): retention time=6.69 minutes.
MS (ES+) 1067 (M+H$^+$, 78%), 1089 (M+Na$^+$, 18).

Description 11
Preparation of Bis-lysine-NTA (D11) (compound of structure III)

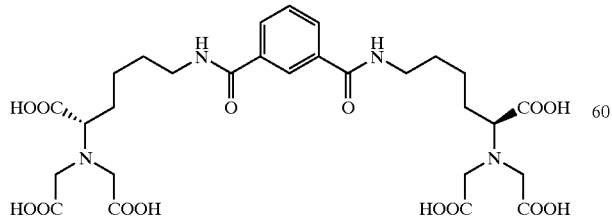

O—(N-succinimidyl)-1,3,3-tetramethyluronium tetrafluoroborate (818 mg, 2.72 mmol) was added to a solution of isophthalic acid (215 mg, 1.29 mmol) in N,N-dimethylformamide (10 ml) and di-iso-propylethylamine (2 ml) at room temperature under Argon and stirred for 15 minutes. N,N-α-bis(carboxymethyl)-(L)-Lysine was added and stirring continued for a further 3 hours. The reaction was quenched by the addition of water and the solvent removed under reduced pressure to afford a residue which was purified by reverse phase preparative HPLC to afford the title compound, after freeze drying, as a colourless solid (750 mg, 89%).
HPLC (analytical): retention time=3.86 minutes; UV (λ max) 260 nm.
$^1$H-NMR (250 MHz, D$_2$O) 7.93 (1H,s), 7.78 (2H, dd, J=7.75 & 1.5 Hz), 7.48 (1H, t, J=7.75 Hz), 4.01 (8H, s), 3.97 (2H, m), 3.31 (4H, t, J=6.25 Hz), 2.00–1.30 (8H, m), 1.21 (4H, dt, J=6.75 & 4.5 Hz).
MS (ES+) 655 (M+H$^+$, 15%), 677 (M+Na$^+$, 22), 693 (M+K$^+$, 25).

Description 12
Preparation of Cinoxacin-(Bis-lysine-NTA) and (Cinoxacin)$_2$-(Bis-lysine-NTA) (D12(a) and D12(b))

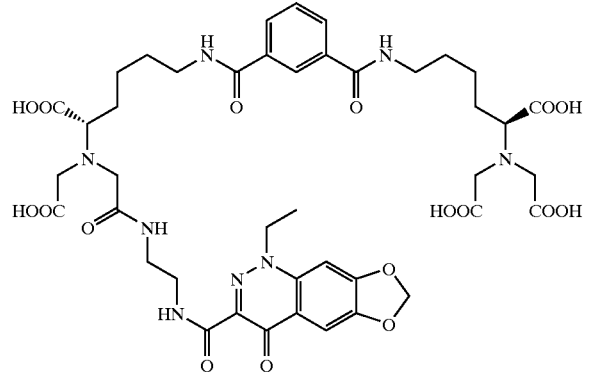

Iso-Butylchloroformate (25 ul, 0.196 mmol) was added to a solution of bis-NTA-lysine (122 mg, 0.186 mmol) in N,N-dimethylformamide (10 ml) and triethylamine (2 ml) and the reaction stirred for 15 minutes N-(2-Aminoethyl) cinoxacin amide (D1) (dissolved in N,N-dimethylformamide (6 ml) and triethylamine (1 ml)) was added dropwise to the solution and stirring continued for 3 hours. The reaction was quenched by the addition of water and the solvent removed under reduced pressure. The residue was purified on reverse phase preparative HPLC to afford the title compounds, after freeze drying, as colourless solids.

Cinoxacin-(Bis-lysine-NTA) (D12(a))—Shown in Structure Above
(55 mg, 31%) HPLC (analytical): retention time=5.93 minutes; UV (λ max) 260, 360 nm.
HPLC (preparative): retention time=6.24 minutes.
MS (ES+) 941 (M+H$^+$, 85%), 963 (M+Na$^+$, 75).

(Cinoxacin)$_2$-(Bis-lysine-NTA) (D12(b))
(37 mg, 32%) HPLC (analytical): retention time=6.77 minutes; UV (λ max) 260, 360 nm.
HPLC (preparative): retention time=6.84 minutes.
MS (ES+) 1227 (M+H$^+$, 38%), 1250 (M+Na$^+$, 20).

SPECTRAL CHARACTERIZATION DATA

Below are some typical excitation and emission spectra, alone with time resolved fluorescence decays for Europium chelates of this invention. All spectra and decay measurements were recorded on an Amino Bowman Spectrophotometer (model AB2), with a time resolution of 50 us.

With reference to FIG. 1, the upper trace shows excitation and emission spectra for Cinoxacin-DTPA (D2) in the presence of $Eu^{3+}$. The characteristic narrow emission bands of europium is observed at around 614 nm. The excitation spectrum for the 614 nm emission band peaks at 355 nm, and at least 50% of this intensity is achieved with excitation wavelengths up to 375 nm. The lower trace shows the fluorescence decay of the chromophore (at 421 nm) and Eu fluorescence (614 nm).

As with the vast majority of fluorescence compounds, the sensitiser group itself has a very short fluorescence lifetime. In fact, the fluorescence lifetime of the chromophore (at 421 nm) was too short to be reliably detected. However, as is clearly shown by the decay traces the fluorescence of the $Eu^{3+}$ incorporated in the chelate (at 614 nm) has a characteristically long lifetime that enables a time-resolved discrimination between the Eu-containing chelate and other fluorescent compounds. The Eu fluorescence lifetime was fitted with a single exponential fit giving a lifetime of 633 us. These data confirm that the Cinoxacin-DTPA chelate exhibits the spectroscopic properties that required for application as a donor label in HTRF-based assays.

Figure 1:
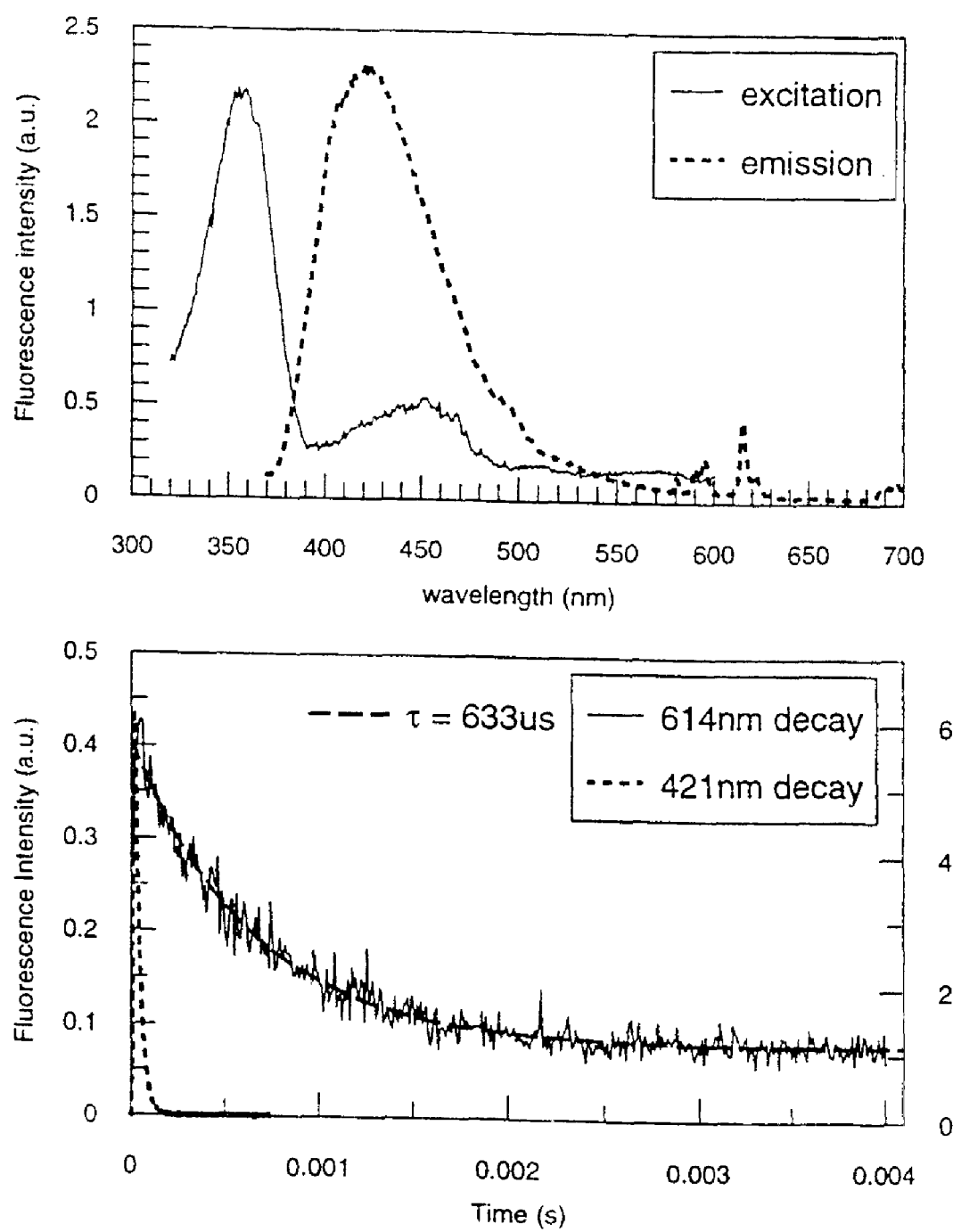
Figure 2:
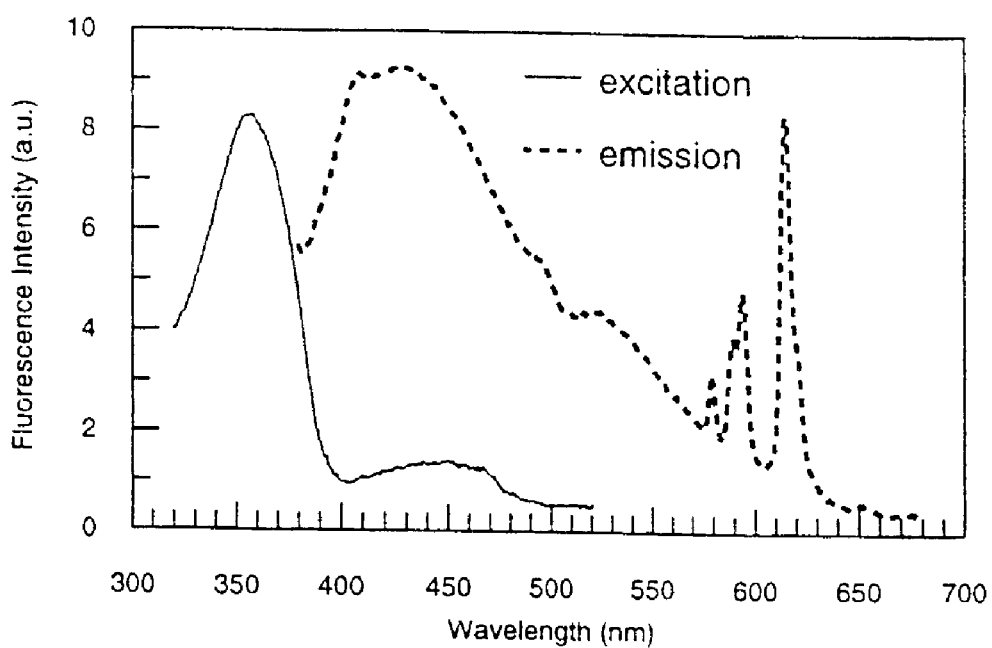
FIG. 2 shows data corresponding to that described in FIG. 1 for Cinoxacin-DTPA-Cinoxacin chelate in the presence of $Eu^{3+}$. Again, the decay of the chromophore (at 430 nm) was too fast for detection.
Figure 2:
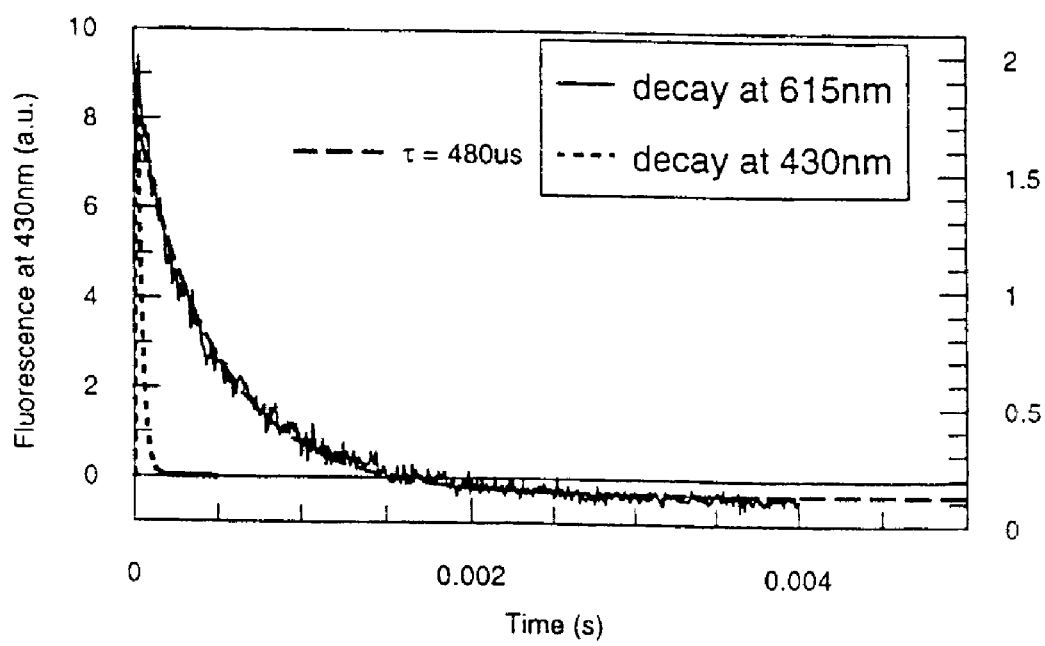
Figure 3:
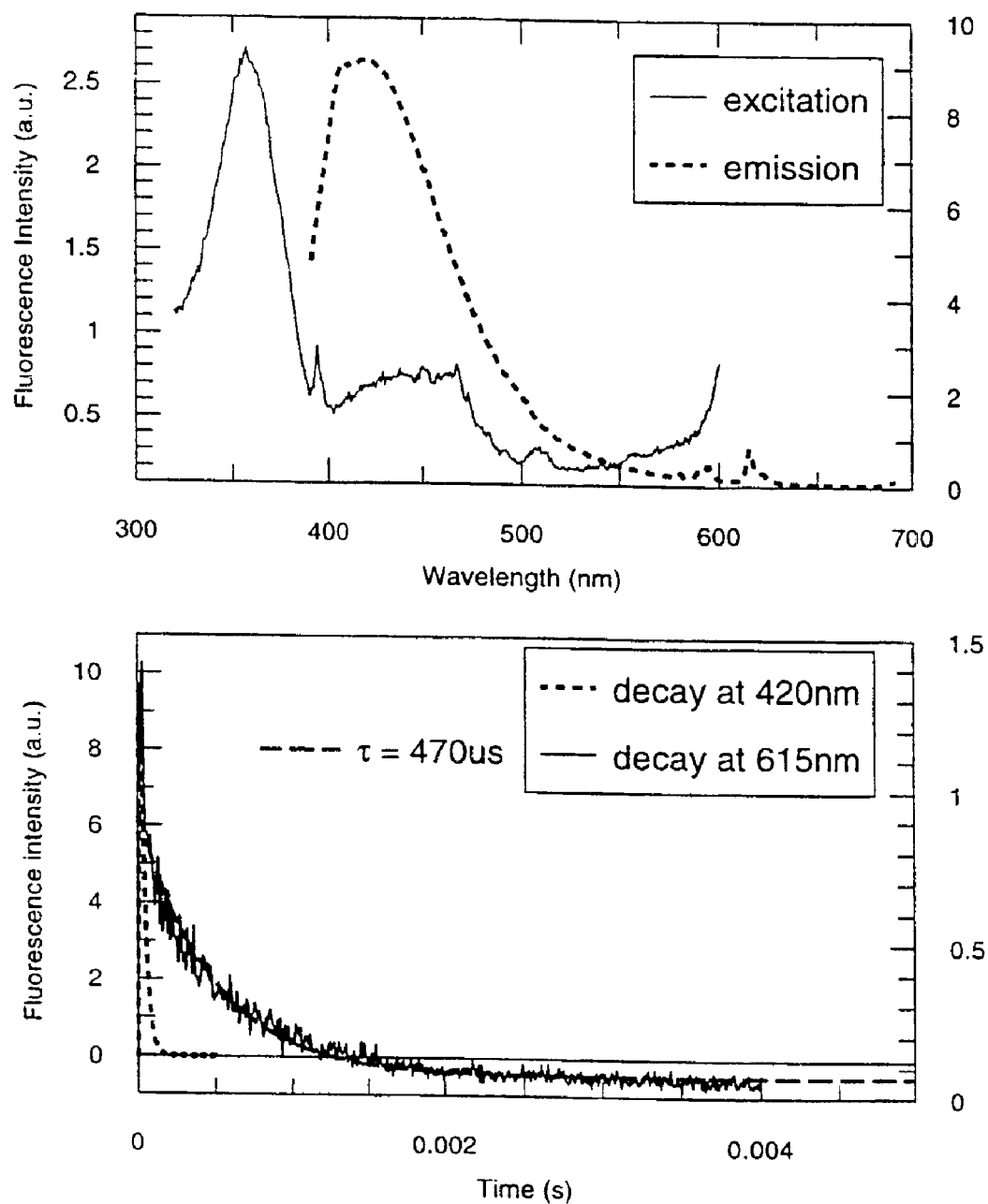
FIG. 3 shows data corresponding to that described in FIG. 1 for Cinoxacin-DTPA-APA-chlorotriazine chelate(D5) in the presence of $Eu^{3+}$.

To assess the "brightness" of the chelates of this invention, their fluorescence intensities were compared, using similar experimental conditions, to a carbostyril chelate (DTPA-CS124) described in WO 96/00901. The Cinoxacin-containing chelates show fluorescence intensities that are comparable with the carbostyril chelates described in the prior art.

Preparation of Cinoxacin-DTPA-APA-$Eu^{3+}$. Streptavidin (Cin-DTPA-SA)

Cinoxacin-DTPA-APA-chlorotriazene (D5) (4 mg) freshly dissolved in 33% v/v DMSO was incubated with 33 uM streptavidin in 100 mM PIPES, pH 7.0 buffer to give molar ratios of streptavidin to chelate of 1:10 and 1:20. Reaction mixtures (500 ul) were incubated for 60 minutes at room temperature and then quenched with 25 ul Tris/HCl to give 50 mM Tris/HCl, pH 8.0 final. To the quenched reaction (525 ul) was added 3×8 ul of 25 mM $EuCl_3$ in water (1.1 mM $Eu^{3+}$) prior to incubation for 30 minutes at room temperature.

The reaction mixtures (549 ul) were then desalted into phosphate buffered saline containing 0.05% Tween 20 (PBS/Tween, Sigma) and 500 ul fractions were collected and assayed for protein content (Coomassie Blue Reagent, Biorad). The concentration of the pooled fractions (2 ml, 14 uM) was determined by Coomassie staining using streptavidin as a standard. The presence of intrinsically fluorescent lanthanide co-elutinly with the protein was demonstrated by observing a time resolved fluorescence signal in the microsecond time gate (400 us delay, 400 us read, cycle time 1000 us, Wallac Victor). 50 nM Cin-DTPA-SA gave 10,000 counts per second in 100 uL using these conditions. Improved labelling conditions yielding brighter conjugates, were obtained by freshly dissolving the Cin-DTPA-APA-chlorotriazine in 100% DMSO, increasing the pH of the reaction mixture to 9.0 in Bicarbonate buffer, and increasing the reaction time to approximately 16 hours at 4° C.

Demonstration of Time Resolved Fluorescence Resonance Energy Transfer from Cin-DTPA-SA to Cy5-Labelled Peptides Cin-DTPA-SA (100 nM) in PBS/Tween was mixed with increasing concentrations (0.1–1000 nM) of N-Succ-(Cy5-NH-K)AERAQAGVVNASSRLAE(K-NH-Biotin)-$CO_2H$ (where underlined letters refer to single amino acid codes) prepared by reaction of the corresponding unlabelled peptide with the N-hydroxysuccinimide esters of biotin and Cy5 (Amersham). After 30 minutes incubation at room temperature, the fluorescence intensity of the sample ($\lambda ex=$ 340 nm, $\lambda em=615$ nm or 664 nm) was determined using a time gate of 400 us, 400 us read time, 1000 us cycle time for europium (615 nm) fluorescence and a time gate of 70 us, 200 us read time, 1000 us cycle time for Cy5 (664 nm) fluorescence. The 615 nm fluorescence decreased in a peptide concentration dependent manner by 62–67% at saturating concentrations of Cy5-peptide whilst the 664 nm fluorescence increased in a saturable manner from 1000 counts/second to 8,000 counts/second at saturating concentration of peptide. Both of these features indicate efficient energy transfer from the Cin-DTPA-SA complex to the fluorescent acceptor. In addition, titration of 10 nM Cin-DTPA-SA with biotinylated allophycocyanin (Bt-APC, 0.5–500 nM, Sigma) in PBS/Tween was associated with an increase in the fluorescence signal at 664 nm from 1000 counts/second to 3,500 counts/second at 500 nM Bt-APC, again indicating energy transfer from the chelate to the acceptor.

Figure 4:
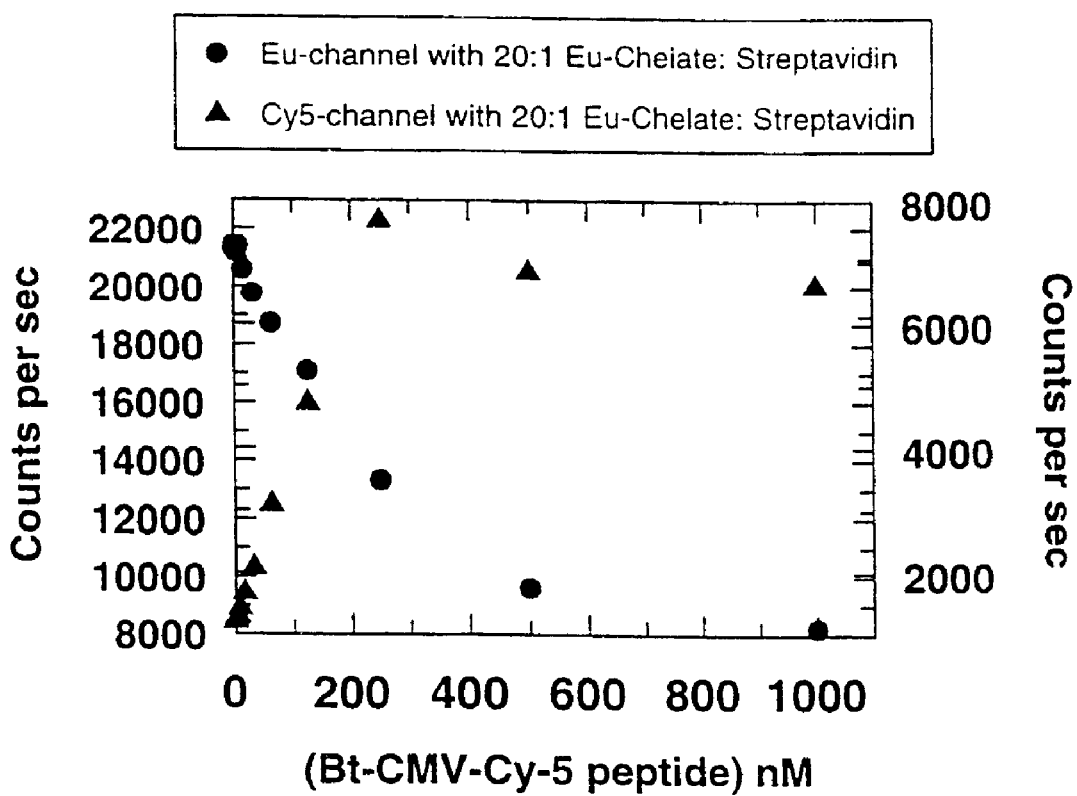

FIG. 4 shows the changes in donor (Eu-chelate) and acceptor (Cy5) fluorescence due to energy transfer. The $Eu^{3+}$ fluorescence decreases and the Cy5 fluorescence increases as the Cy5-labelled peptide is titrated in. The energy transfer occurs as the Eu and Cy5 are brought in proximity by the streptavidin-biotin interaction.

What is claimed is:

1. A lanthanide chelate comprising one or more sensitiser groups covalently attached to a lanthanide chelating group, wherein the sensitiser group is of formula (I)

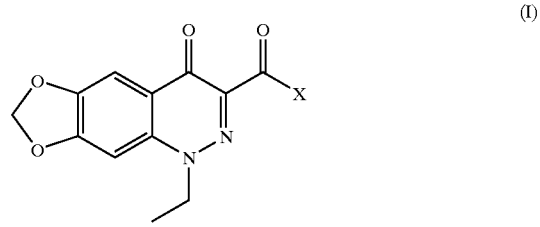

(I)

where X is a group that couples the said sensitiser group to the said chelating group.

2. A lanthanide chelate according to claim 1 in which X is —$NH(CH_2)pNH$—, wherein p is 2, 3 or 4 and which forms an amide bond with the chelating group.

3. A lanthanide chelate according to claim 1 in which the chelating group is selected from the group consisting of a moiety of formula (II)

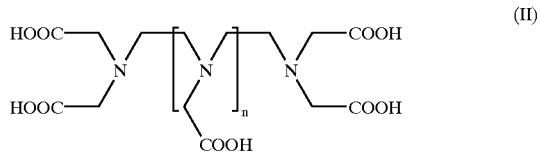

(II)

where n is 1 (DTPA) or 2 (TTHA) or a group of formula (III)

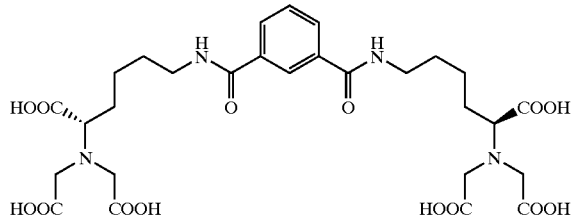

(III)

4. A lanthanide chelate according to claims 1 to 3 further comprising a linker group which is also covalently bonded to the chelating group wherein the linker group is a group of formula (V)

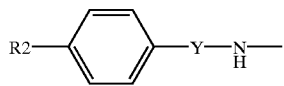

(V)

in which Y is $CH_2$, $CH_2CH_2$ or —$CH_2CH(COOH)$— and $R^2$ is a reactive group which is suitable for derivatising macromolecules;
or the linker group is a group of formula (VI)

(VI)

in which n is 1 to 5, Z is a bond or a group —$CH_2CH$(COOH)— and $R^2$ is as defined for formula (V).

5. A lanthanide chelate according to claim 4 in which the group $R^2$ is selected from the group consisting of: an amine reactive group, a thiol reactive group or a photoactivatable reactive group.

* * * * *